United States Patent [19]

Pozuelo

[11] 4,124,715

[45] Nov. 7, 1978

[54] METHOD OF PHARMACOLOGICALLY TREATING DRUG ADDICTION WITH FUSARIC ACID

[76] Inventor: Jose Pozuelo, 1463 Burlington, Cleveland Hts., Ohio 44118

[21] Appl. No.: 797,410

[22] Filed: May 16, 1977

[51] Int. Cl.$^2$ .......................................... A61K 31/455
[52] U.S. Cl. .................................................... 424/266
[58] Field of Search ....................................... 424/266

[56] References Cited

U.S. PATENT DOCUMENTS 3,903,285  9/1975  Umezawa et al. ................... 424/266

OTHER PUBLICATIONS

Chem. Abst. 78-7826 t (1973).

Primary Examiner—Stanley J. Friedman
Attorney, Agent, or Firm—Fay & Sharpe

[57] ABSTRACT

A method of pharmacologically alleviating craving for and withdrawal from narcotics and amphetamines in human beings which method comprises administering to a human being a therapeutically effective amount of fusaric acid (5-butyl-picolinic acid). Pharmaceutical compositions adapted for use in the foregoing method are also provided.

2 Claims, No Drawings

METHOD OF PHARMACOLOGICALLY TREATING DRUG ADDICTION WITH FUSARIC ACID

BACKGROUND OF THE INVENTION

The present invention relates to a method of overcoming the problems associated with treating patients who are addicted to narcotics and/or amphetamines. More specifically, it relates to a means of pharmacologically abolishing the craving and the withdrawal syndrome normally experienced when a patient is deprived of such narcotics and/or amphetamines.

As above noted, two major aspects of the treatment of the individual drug addict relate to abolishing the craving and dependence, be they psychological or physical, and to the prevention of the withdrawal or abstinence syndrome. Attempts to accomplish these objectives in a pharmacological manner can be considered in two major categories: the replacement of the offending drug with one more acceptable, even if still addictive, and the use of compounds that may alter the biochemical basis of addiction and withdrawal symptoms.

Various pharmacological approaches for treating narcotic and/or amphetamine addiction have been tried in the past. However, while certain of such approaches have been successful in varying degrees, each such approach has certain limitations and drawbacks. For example, previous experimental work in morphine addicted monkeys has demonstrated that treatment with alpha-methyl-para-tyrosine abolished the craving for morphine and diminished or abolished the manifestations of the abstinence syndrome. The results of this investigation suggested that alpha-methyl-para-tyrosine could be used in the treatment of narcotic and amphetamine addictions and other mental conditions where the catecholamines were known to play a fundamental role.

The results of these experiments led, in 1972, to the trial of alpha-methyl-para-tyrosine in patients addicted to morphine. Unfortunately, they all developed alpha-methyl-para-tyrosine crystalluria, as in retrospect, had the monkeys, and treatment was discontinued.

Accordingly, the main object of the present invention is to provide an alternative method for treating patients suffering from addiction to narcotics and/or amphetamines without the formation of crystalluria or other undesirable side-effects.

Another object of the present invention is to provide a composition which is especially adapted to be used in the above-described method.

Other objects will be apparent to those skilled in the art from a reading of the following description and claims.

SUMMARY OF THE INVENTION

The present invention provides a safe and effective method of alleviating the craving and withdrawal syndrome associated with the treatment of persons addicted to narcotics and/or amphetamines. Broadly, this is accomplished by administering to an addicted person a therapeutically effective amount of fusaric acid (5-butyl-picolinic acid).

In another aspect, the present invention concerns a pharmaceutical composition which is used in the practice of the foregoing method. This composition comprises a pharmaceutical preparation in dosage unit form which includes the desired amount of fusaric acid (5-butyl-picolinic acid).

DESCRIPTION OF THE PREFERRED EMBODIMENTS OF THE INVENTION

The present invention concerns the use of fusaric acid (5-butyl-picolinic acid) in the treatment of narcotic and amphetamine addiction. This compound is sometimes herein identified simply by its common name, fusaric acid. It has the following structural formula:

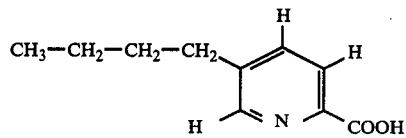

In the practice of the present invention fusaric acid is administered in a therapeutic amount. That is, the person being treated is given increasing amounts of the concerned compound until craving and withdrawal syndrome are no longer observed. The exact amount to be utilized varies from person to person. The exact amount required is correlated to the degree of addiction and is determined empirically. However, in practice fusaric acid is usually administered in amounts ranging from about 8 to about 20 mgs per kilogram of body weight per day.

Fusaric acid can be administered in various ways. For example, it can be given in pill or capsule form, with or without a filler or other ingredients. It can be given in a solid, liquid or semi-liquid state. If desired, it can be administered intravenously. In such a case, it is simply dissolved or suspended in a suitable solvent or carrier and the pH of the fusaric acid solution adjusted to 7.0 with 1N NaOH solution.

As above noted, fusaric acid can be mixed with other materials. For example, in the case of a tablet, the composition can also include, fillers, binders, and diluents such as lactose, metylcellulose, talc, gum tragancanth, gum acacia, agar, polyvinylpyrrolidone, calcium stearate, and/or corn starch, etc. In the case of a liquid solution or suspension for oral administration, the composition can include, a filler such as sodium carboxymethylcellulose and/or syrup, e.g., a glycerine based syrup. In the case of a parenteral solution, the composition will comprise, a suitable solvent or other liquid such as a saline solution with the pH adjusted to pH of 7 with NaOH.

The practice of the present invention is further exemplified by the following general discussion and case studies.

Two patients with well documented histories of addiction and dependence on various narcotics and amphetamines submitted voluntarily in the initial study designed to show the effectiveness of the present invention. One of the patients had severe, chronic amphetamine addiction. The other patient was a severe methadone and pentazocine addict as a consequence of chronic postoperative pain.

These patients were transferred from the drugs they were taking to satisfy their craving and prevent the manifestations of abstinence to regular doses of morphine or amphetamines every 3 to 4 hours during the day and spaced every 4 to 6 hours at night. A baseline of the daily requirement of morphine for each patient, as measured by the amount of morphine needed to satisfy the craving and to prevent the manifestations of abstinence was established for the narcotic addicted patient. A period of a week was used for each patient, not only to confirm the morphine requirement, but also to study catecholamine levels urinary pH, and other constants (vital signs, blood pressure, respiral, electrolytes).

The patient dependent on narcotics was transferred to an equivalent dose of morphine. A baseline of the daily requirement of morphine for the patient, as measured by the amount of morphine needed to satisfy the craving and to prevent the manifestations of abstinence was established. A period of a week was used for the patient, not only to confirm the morphine requirement, but also to study catecholamine levels, urinary pH, and other constants.

After this initial study, another six patients have been treated with fusaric acid with similar results.

Fusaric acid was started after the baseline was determined, and increased gradually until either a therapeutic level was reached, as measured by the lack of desire of the patient to have narcotics or amphetamines, or previously established maximum doses of fusaric acid were reached. The starting dose of fusaric acid was 5 mg/kg of body weight per day given in four divided doses.

Urine specimens of the patients receiving fusaric acid were checked daily to see if any crystals of fusaric acid were present. None were found.

The morphine addicted patients were maintained on regular doses of morphine, and amphetamine dependent patients on 40 to 60 mg amphetamine per day to prevent a rebound of amphetamine depression without causing an amphetamine psychosis.

In the narcotic addicted patients, when the dosage of fusaric acid administered orally was close to 10 mg/kg of body weight per day, the regular dosage of morphine was discontinued and given only at the patient's request. For the amphetamine dependent patients, amphetamines were discontinued after reaching a daily dose of 15 mg fusaric acid/kg body weight. The patients were told that the amphetamines or morphine would be given if they still craved them.

CASE REPORTS

Case 1. A 35-year-old, married woman had a chronic history of amphetamine addition that had started at age 18 to curb her appetite and to overcome feelings of depression. She had reached the point of consuming 200 mg dextroamphetamine a day, and other addicting compounds for headaches and general aching. She had needed as much as 40 to 50 mg of dextroamphetamine to start work in the morning and continued taking 20 to 30 mg of amphetamines every 2 to 3 hours to "keep going" during the day. To sleep at night she resorted to various barbiturates.

The patient consulted several psychiatrists and other physicians to obtain relief of her aches and was hospitalized twice in order to treat her dependence. Every attempt to cure her addiction and withdraw the amphetamines had failed.

She was admitted to our study and once the baseline was established she was started on 250 mg fusaric acid per day.

After a dosage of 1000 mg fusaric acid a day was reached the amphetamines were discontinued and the patient never requested them again. Her generalized aches, fatigue, chronic pain, and headaches disappeared and she was discharged 15 days after the start of fusaric acid therapy. She no longer required amphetamines and had no craving or desire for them. One week after discharge from the hospital she reported that while she was still maintained on 750 mg per day of fusaric acid she had a "nauseous feeling" at the mere thought of amphetamines.

Case 2. A 58-year-old housewife had a history of severe depression in her 30s after she underwent a hysterectomy. She had a lumbar disc removed 9 years ago and since then has needed various medications for relief of pain. Four years ago she had a spinal fusion because of persistent lumbar pain. However, the operation failed to relieve her pain and two other back operations were performed.

A well documented history of narcotic intake dates back 4 years, to the time of the spinal fusion, when methadone or pentazocine intramuscularly were prescribed. She alternated with whatever substitute was available by using different prescriptions. She was admitted to hospitals several times seeking relief of pain but never was withdrawn from narcotics, because among other things the amount she was taking never was discovered. Recently, she was taking 3 ampules of methadone (50 mg) or pentazocine (120 mg) in a single injection 4 to 6 times a day for relief of pain in her legs.

To compensate for her methadone and pentazocine dependence she needed about 250 to 300 mg daily of morphine in 6 to 8 divided doses to satisfy her craving and to prevent the initiation of withdrawal between injections.

Fusaric acid was prescribed after a baseline of morphine requirements to compensate her methadone dependence was established. The amount of fusaric acid was increased gradually from 350 to 1200 mg a day in six divided doses. The requests for morphine gradually decreased and on the 18th day after fusaric acid treatment was initiated she stopped taking morphine and was free of her chronic pain.

Eight days after the patient stopped taking morphine, while receiving a dose of 1000 mg of fusaric acid, she started to manifest symptoms of endogenous depression which responded to treatment with imipramine. It is difficult to say whether this depression was related to her makeup and previous depressive episodes or to the intake of fusaric acid and consequent depletion of norepinephrine. However, neither the craving for morphine nor the manifestation of withdrawal has returned.

Numerous other patients addicted to such drugs as amphetamines, heroin, methadone and methadone-pentazocine have also been treated with fusaric acid in accordance with the teachings of the present invention. All such patients were free from craving or withdrawal symptoms.

The results obtained in this study indicate that fusaric acid is effective in abolishing the craving for morphine and amphetamines, and in preventing manifestations of withdrawal in human addicts. The fact that the morphine and amphetamines were readily available at the patients request and that the patients rejected them because the craving had disappeared, and there were no manifestations of withdrawal lends further support to this study which shows the effectiveness of the fusaric acid in the treatment of narcotic and/or amphetamine addiction in humans.

The effects of fusaric acid are thought to be due, in the main, to the inhibition of catecholamine synthesis and consequent decreased content of catecholamines in the brain. However, the present invention is not necessarily directed to this mechanism but to a means for alleviating craving and withdrawal syndrome experienced by narcotic and amphetamine addicts.

While there have been described what are at present considered to be the preferred embodiments of this invention, it will be obvious to those skilled in the art that various changes and modifications may be made therein without departing from the invention, and it is, therefore, aimed in the appended claims to cover all such changes and modifications as fall within the true spirit and scope of the invention.

What is claimed is:

1. A pharmacological method of alleviating craving for and withdrawal from narcotics and amphetamines in addicted human beings said method comprising:
   administering to a human being addicted to narcotics or amphetamines a therapeutically effective amount of a compound having the following structural formula:

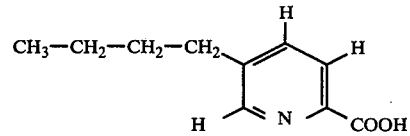

2. The method of claim 1 wherein said compound is administered in an amount ranging from 8 mg/kg body weight/day to about 20 mg/kg body weight/day.